United States Patent [19]

Guenther et al.

[11] Patent Number: 4,856,038

[45] Date of Patent: Aug. 8, 1989

[54] DENTAL X-RAY DIAGNOSTICS INSTALLATION FOR PRODUCING PANORAMIC EXPOSURES OF SLICES IN THE SKULL

[75] Inventors: Werner Guenther; Erich Heubeck; Manfred Muether, all of Bensheim, Fed. Rep. of Germany

[73] Assignee: Siemens Aktiengesellschaft, Berlin and Munich, Fed. Rep. of Germany

[21] Appl. No.: 101,722

[22] Filed: Sep. 28, 1987

[30] Foreign Application Priority Data

Sep. 26, 1986 [DE] Fed. Rep. of Germany ....... 3632817

[51] Int. Cl.⁴ ................................................ A61B 6/14
[52] U.S. Cl. ....................................... 378/39; 378/21; 378/40; 378/99
[58] Field of Search ..................... 378/21–27, 378/38–40, 99; 358/111

[56] References Cited

U.S. PATENT DOCUMENTS

| | | | |
|---|---|---|---|
| 3,283,147 | 11/1966 | Avakian | 250/494.1 |
| 4,039,837 | 8/1977 | Ohta | 378/39 |
| 4,418,419 | 11/1983 | Schreiber et al. | 378/40 |
| 4,609,940 | 9/1986 | Born et al. | 378/99 |
| 4,624,007 | 11/1986 | Muranushi | 378/99 |
| 4,649,555 | 3/1987 | Matsubayashi | 378/99 |

FOREIGN PATENT DOCUMENTS

| | | |
|---|---|---|
| 0035307 | 9/1981 | European Pat. Off. . |
| 0087946 | 9/1983 | European Pat. Off. . |
| 2116705 | 10/1972 | Fed. Rep. of Germany ........ 378/21 |
| 3007935 | 9/1981 | Fed. Rep. of Germany . |
| 3227784 | 2/1984 | Fed. Rep. of Germany . |
| 2151842 | 3/1973 | France . |
| 2393496 | 2/1979 | France ................................... 378/99 |

Primary Examiner—Craig E. Church
Assistant Examiner—John C. Freeman

[57] ABSTRACT

A dental x-ray diagnostic installation for the production of panoramic exposures of slices of the skull of the patient particularly in the region of the jaw, characterized by an exposure unit with an x-ray unit pivotable around an axis and displaceable in a plane perpendicular to the axis, a film holder unit lying opposite and moveable relative to the x-ray unit, a head holder arranged between the two units, a control arrangement for controlling the pivoting and displacement movement of the exposure unit relative to the head holder and also controlling the movement of the film holder relative to the x-ray tube of the exposure means and an input arrangement for inputting of information of the selected curvature of the slice being exposed. The improvements are that the input means is constructed so that the curvature of the slice to be exposed can be directly graphically inputted into the control arrangement such as by means of a monitor with a light pen or by means of a "computer graphic tablet".

10 Claims, 3 Drawing Sheets

DENTAL X-RAY DIAGNOSTICS INSTALLATION FOR PRODUCING PANORAMIC EXPOSURES OF SLICES IN THE SKULL

BACKGROUND OF THE INVENTION

The present invention is directed to a dental x-ray diagnostics installation for producing overview pictures or panoramic exposures of slices of the skull of the patient, particularly in the region of the jaw. The installation includes an x-ray tube pivotable around an axis and displaceable in a plane proceeding perpendicular to the axis, a film holder lying opposite the exposure unit and movable relative thereto, a head holding arrangement for holding the head on the axis between the two units and a control arrangement or means which first controls the pivoting and displacement motion of the exposure unit relative to the head holder and secondly controls the movement of the film holder relative to the x-ray tube, so that different slices of the skull can be exposed and the path of the respective slices to be exposed is selectable on the basis of input means.

U.S. Pat. No. 4,418,419 which claims priority from German Application No. 30 07 935 and which disclosure is incorporated by reference thereto, discloses an x-ray dental diagnostic installation or dental tomographic apparatus wherein an x-ray unit and film holder pivot around a first axis and are displaceable in a plane perpendicular to said first axis to take dental panoramic radiographs. In the known x-ray diagnostic installation, the input means comprises a member introducable into the mouth of the patient, which is provided with a plurality of pressure contacts which are activated by biting of the input means by the patient. The switch condition of the pressure contacts produces signals for a control means which allows the movement of the exposure unit and the film holder to be controlled during the exposure so that a slice or path proceeding through the actual pressure contacts in the region of the jaw of the patient is exposed. Under the precondition that the patient has normal tooth alignment, the known x-ray diagnostics installation will allow high quality panoramic radiographs of slices that proceed in the region of the jaw of the patient to be produced. However, when the patient has even a slight malalignment of the teeth, a faultless exposure quality in the region of the dental roots is no longer guaranteed with certainty. When serious malalignments of the teeth are present, there is a risk that the individual teeth of the patient will not be sharply imaged due to the fact that only relatively few pressure contacts are present. Moreover, the overview exposure of, for example, temporomandibular slice or the slices proceeding in the region of the maxillary sinus cannot be produced with the known x-ray diagnostic installation because the path of the slice is dependent on the shape of the teeth of the patient due to the fashioning of the input means as mentioned hereinabove.

SUMMARY OF THE INVENTION

The object of the present invention is to provide a dental x-ray diagnostic installation in which high quality panoramic exposures or overview exposures can be produced given dental malalignments of the patient and, moreover, panoramic exposures of the slices which arbitrarily proceed in the skull can be produced independent of the shape of the teeth and jaw of the patient.

These goals and objects are achieved in an improvement in a dental x-ray diagnostic installation for the production of panoramic exposures of slices of a skull particularly in the region of the jaw. The installation comprises an exposure unit with an x-ray tube being mounted to pivot around an axis and being mounted for displacement in a plane proceeding perpendicular to the axis, a film holder unit lying opposite the exposure unit and being moveable relative thereto, a support means holding a head between the two units, and control means for first controlling the pivot and displacement motion of the exposure unit relative to the support means and for record controlling the movement of film holder relative to the x-ray tube, said control unit includes input means for selecting a curvature of a slice to be exposed so that the curvature means controls the movement for the path or curve of the slice being selected. The improvement is that the input means is constructed as a graphical input means in which the curvature of the slice to be exposed can be directly graphically inputted into the installation.

The direct graphical input is that the input means is positioned to acquire the curvature of the layer to be exposed which is present as a continuous curve and this slice is thus capable of being arbitrarily selected regardless of the shape of the teeth and jaw and takes consideration of malalignments of the teeth of the patient.

The direct graphical input can occur in especially expedient manner when the input means in accordance with a modification of the invention comprises what is referred to as a "Computer graphic tablet" or a monitor comprising a light pen. In these two modifications, the course or curvature of the slice to be exposed can be recorded directly on the touch sensitive surface of the "Computer graphic tablet" with a standard pen or writing instrument or with the light pen and/or a sheet of paper lying on the picture screen of the monitor. It is expedient in both instances to provide a line grid in order to guarantee an observation of certain size ratios. In the frame work of the invention, however, the input means can also comprise other means, for example what is referred to as a digitizer, which optically or mechanically allows an original or model for the desired curvature of the slice to be sensed, for example a curve recorded on paper and corresponding to the curvature of the slice to be exposed.

In order to enable the visual supervision of the input curvature of the slice to be exposed, the input means in a modification of the invention comprises means for graphically illustrating the curvature of the slice to exposed. When the input means comprises a monitor with a light pen, the input curvature can be portrayed on the monitor itself. When the input means comprises a "computer graphic tablet" or other means for inputting the curvature of the slice to be exposed, the means for the graphic portrayal thereof can be formed by additionally providing a monitor, plotter or printer.

In accordance with the embodiment of the invention, a memory is provided in which data on one or more curvatures of slices to be exposed can be stored. These stored curvatures are suppliable both to the input means for the graphic portrayal of the curvature of slices to be exposed as well as to the control means for producing corresponding exposures whereby one part of the memory can also be executed as a read-only memory in which the data of the plurality of standard curvatures of slices to be exposed are stored. It is then possible to retrieve curves of slices to be exposed which belong to specific patients as needed in order, for example, to be able to monitor the success of the jaw or dental orthopedic treatment or, respectively, in the case of patients who exhibit no anomalies with respect to the shape of their teeth and tooth alignment, to be able to produce the panoramic exposure without having to again input a curvature of a slice to be exposed which corresponds to the standard curvature in the case of many patients. What is achieved by storing the standard curvatures in a read-only memory is that these standard curvatures cannot inadvertently be lost due to erasures or overwriting.

An especially comfortable operation of the x-ray diagnostics installation is achieved when the means of the input device for the graphic portrayal of curvatures of the slice to be exposed are fashioned so that a plurality of curvatures of slices to be exposed can be simultaneously graphically portrayed and the input means itself is fashioned so that one of the illustrated curvatures of slices to be exposed can be directly selected for the production of a corresponding exposure or picture. When the input means comprises a monitor with a light pen, this means that a plurality of curvatures of slices to be exposed are portrayed on the monitor and that the curvature suitable for the production of the following exposure or picture can be selected by tapping with the light pen.

In order to proceed on the basis of input curves or curvatures of a slice to be exposed, and to be able to produce corresponding panoramic exposures, an embodiment of the invention provides a computation means, which converts a curve of a slice to be exposed which is inputted into the input means into preferably digital data for the control means. The computation means can also serve the purpose of identifying the curvature of the appertaining, sharply imageable layer thickness proceeding on the basis of the curvature of the slice to be exposed whereby the means for the graphic portrayal of the curvature of the slices to be exposed then additionally illustrates these thicknesses in addition to the actual curvature of the slice to be exposed.

Proceeding on the basis of the curvature of a slice to be exposed, the computation means can also serve the purpose of processing this curvature in the sense of either a compression or expansion. Thus the input means can be utilized to acquire the curvature which is to be exposed. It is thus possible to vary curvatures of slices to be exposed which have already been inputted and to adapt them to the respective requirements.

Other objects and advantages of the present invention will be readily apparent from the following description of the preferred embodiments, the drawings and claims.

DESCRIPTION OF PREFERRED EMBODIMENTS

Figure 1:
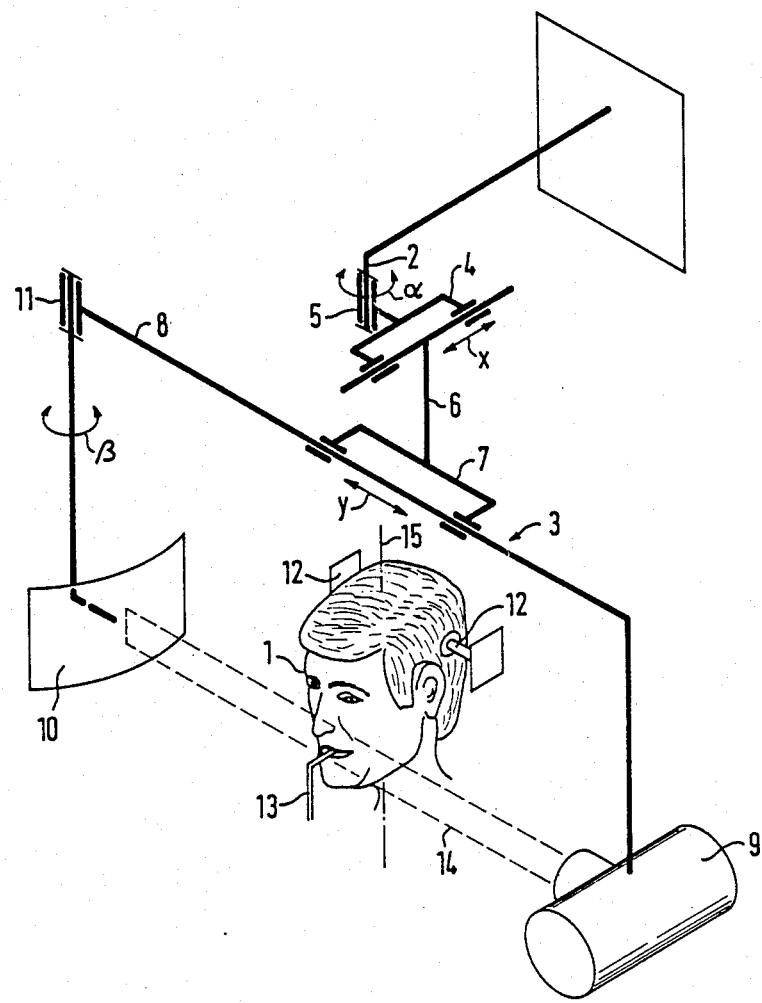
FIG. 1 is a schematic, perspective view of a mechanical structure of an x-ray diagnostic installation in accordance with the present invention.

The principles for this invention are particularly useful in a dental x-ray diagnostic installation schematically illustrated in FIG. 1 for use in producing overview exposes of slices or panoramic exposures of the slice proceeding in the skull 1 of a patient, particularly in the region of the jaw. The installation comprising an exposure unit 3 which pivots around a axis 2 in the direction of a double arrow $\alpha$. This exposure unit 3 also is displaceable in the direction of the double arrows x and y which are in a plane that extends perpendicular to the axis 2. For this purpose a longitudinal guide 4 is arranged in a plane proceeding a right angle relative to the axis 2 and is attached to the axis 2 with a bearing 5 so as to pivot or rotate in the direction of the double arrow $\alpha$. An intermediate part 6 is accepted in the longitudinal guide 4 for displacement in the direction of the double arrow x, and this intermediate part 6 in turn carries a longitudinal guide 7 which is arranged in a plane proceeding at right angles relative the axis 2 and is offset by 90° relative to the longitudinal guide 4. A carrier 8 of the exposure unit 3 is accepted in the longitudinal guide 7 and is displaceable in the direction of the double arrow y. The longitudinal guides 4 and 7 are constructed so that they only allow longitudinal but not pivotal or rotational movement of the intermediate part 6 and of the carrier part 8. In other words, they can be provided with a spline arrangement so that only an axial movement is allowed. The carrier 8 at a first end has an x-ray unit 9. At a second or other end, a film holder 10 is connected to the carrier 8 by mounting means including a bearing 11 which allows rotation of the film holder in the direction of the double arrow $\beta$. Support means for holding the skull 1 of the patient are arranged between the x-ray tube 9 and the semicircular film holder 10. The support means comprises a head support 12 and a bite-down part 13 which co-act to hold the skull of the patient stationary and in a given position relative to the unit 9 during the production of an exposure.

For producing an panoramic exposure, an x-ray beam 14 emerging from a slit diaphragm of the x-ray tube or radiation source 9 and having a slit like cross section that proceeds parallel to the axis 2 is sent through the skull 1 of the patient. In order to achieve the desired course or path of the slice to be exposed in the skull, the exposure unit 3 is displaced in the direction of the double arrows x and y in the plane that extends at right angles relative to the axis 2. Displaced with the longitudinal guides 4 and 7 causes the exposure unit 3 to rotate around a momentary axis 15 which due to the displacement in the guides and the rotation around the axis 2 follows a path which corresponds to the curvature of the slice to be exposed. The movement of the exposure unit 3 occurs so that the x-ray beam 14 perpendicularly penetrates the respective region to be exposed of the curvature of the slice to be exposed. At the same time, the film holder is rotated or pivoted in a direction opposite to the pivot motion of the exposure unit 3 with the speed of rotation being such that the path speed of the film is proportional to the respective speed of the momentary axis 15 so that a constant magnification along a curvature of the slice to be exposed will occur. The movement of the exposure unit 3 in the direction of the double arrows x, y and $\alpha$ as well as the movement of the film holder in the direction of the double arrow $\beta$ are effected by respective stepping motors $M_x$, $M_y$, $M_\alpha$ and $M_\beta$ (FIGS. 2 and 3).

Figure 2:
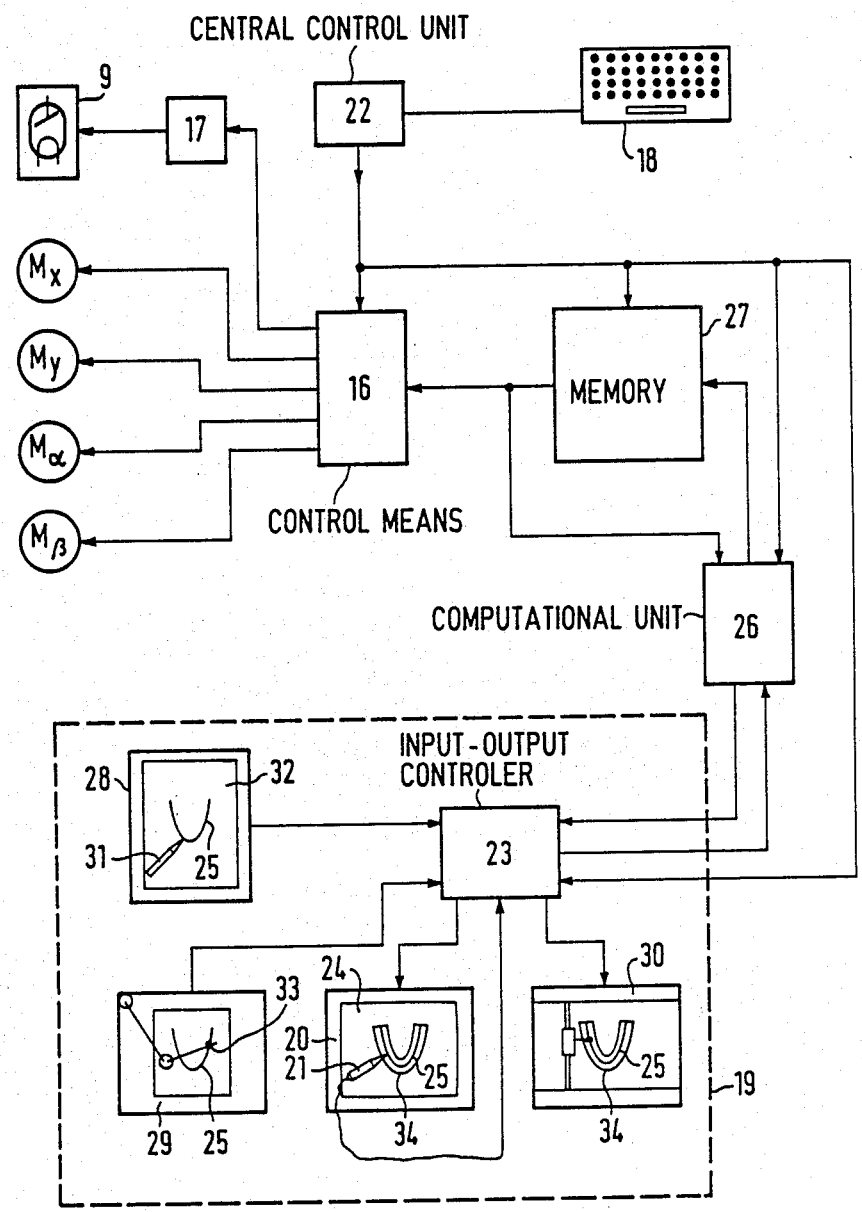
FIG. 2 is a block circuit diagram of an x-ray diagnostic installation of the present invention.
Figure 3:
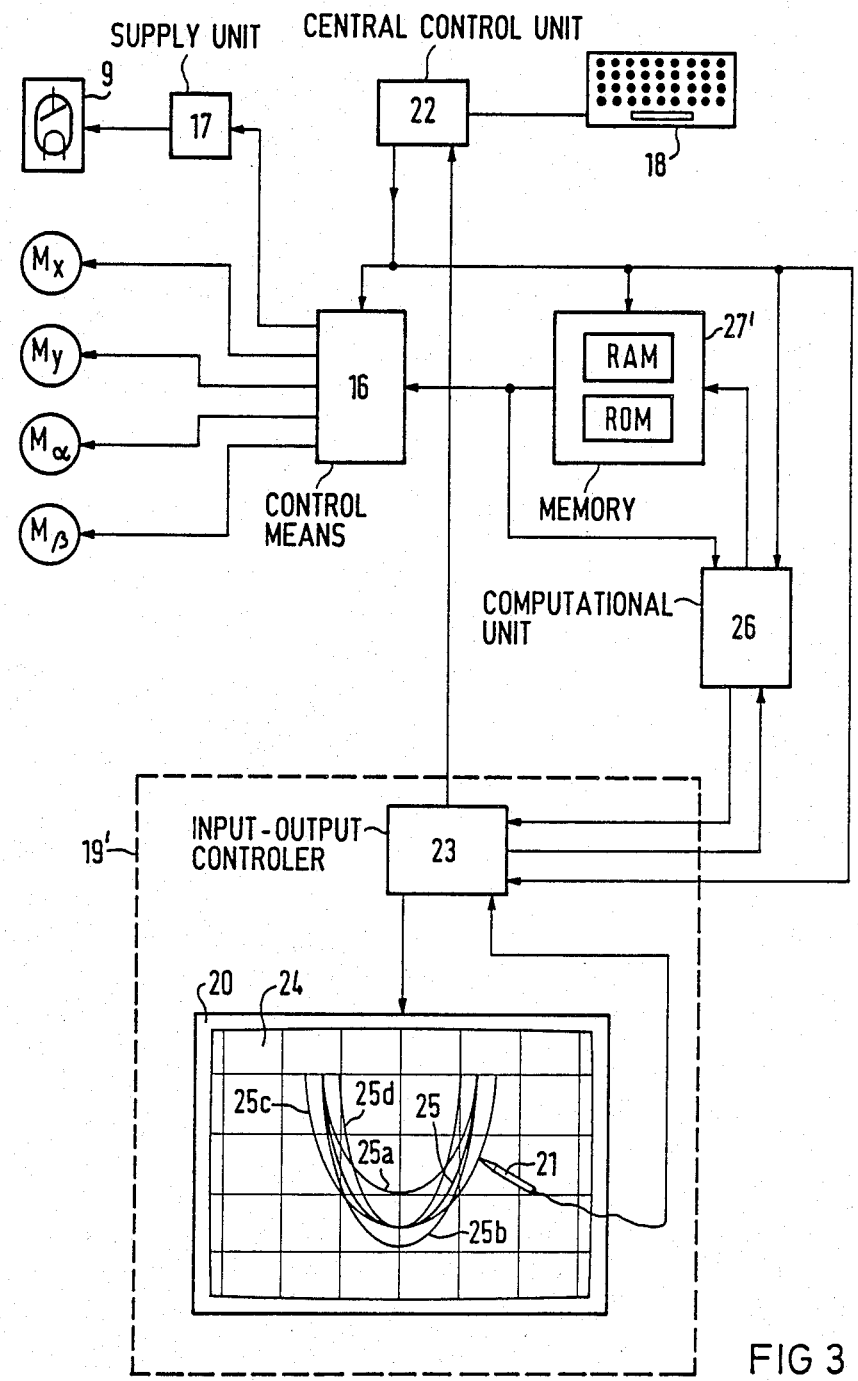
FIG. 3 is a block circuit diagram of a modification of a x-ray diagnostic installation of the present invention.

The stepping motors $M_x$, $M_y$, $M_\alpha$ and $M_\beta$ are schematically illustrated in FIG. 2 which shows a block circuit diagram of an x-ray diagnostic installation of the invention which is operated by a control means 16. A power supply unit 17 for the x-ray tube is also illustrated. The control means 16 is in communication with the central control unit 22 for instance microprocessor 80 186 Siemens which is operable by a keyboard for instance 7030 ASCII—coded firm Marquardt 18. In addition, the x-ray diagnostics installation of the invention has an input means 19 which comprises among other things a monitor 20 with a light pen 21 which are both connected to an input-output controller 23. For instance CRT controller 8275H, Intel. The curvature 25 for a slice to be exposed is recorded on the picture screen of the monitor 20 with the light pen 21 and input controller 23 portrays the path or curvature 25 on the picture screen 24 of the monitor. In addition the input controller 23 communicates the electrical signal corresponding to the curvature 25 of the slice to be exposed to a computation unit 26 for instance microcontroller 80C51 Siemens which converts these electrical signals into signals, particularly digital signals suitable for the control means 16 and forwards them to a memory 27 which initially stores these digital signals. The memory 27, for instance memory 27C256, Intel 15.9, is connected to the control means 16 and to the central control unit 22.

For producing an overview exposure or panoramic exposure corresponding to the input curvature 25 of a slice to be exposed, one proceeds so that the skull 1 of the patient is first fixed in a position suitable for the exposure of the desired slice. This positioning is done with a head support 12 and with the bite-down part 13 (FIG. 1). After a suitable actuation of the keyboard 18, the central control unit then calls in the data from the memory 27 which corresponds to the starting point for the curvature 25 of the slice to be exposed. The data is supplied to the control means 16 which in turn actuates the stepping motors, $M_x$, $M_y$, $M_\alpha$ and $M_\beta$ so that the exposure unit 3 and the film holder 10 will assume a starting position corresponding to the curvature 25 of the slice to be exposed. In response to the addition and suitable actuation of the keyboard 18, the central control unit 22 initializes or starts the control means 16 to place the x-ray tube 9 in operation. At the same time, the central control means 22 causes a continuous transmission of data corresponding to the curvature of the slice to be exposed into the control means 16 which in turn actuates the stepping motors $M_x$, $M_y$, $M_\alpha$, and $M_\beta$ so that the exposure unit 3 and the film holders 10 execute the movements required for the production of the panoramic exposure. As soon as the exposure unit 3 and the film holder 10 have reached their final positions corresponding to the curvature of the slice to be exposed, the x-ray unit is shut off.

In addition to the monitor 20 with the light pen 21, the input means 19 of the x-ray diagnostic installation of the invention shown in FIG. 2 also has a "computer graphic tablet" 28 of a conventional design, a digitizer 29 of a conventional design. The computer graphic tablet 28 and digitizer 29 are optionally available for the inputting of the curvature 25 of the slice to be recorded instead of the monitor 20 with the light pen. In response to a suitable actuation of the keyboard 18, the central control unit 22 will actuate the input-output controller 23 to enter into communication either with the monitor 20, with the light pen 21, with the "computer graphic tablet" 28 or with a digitizer 28 for inputting the curvature of the slice to be exposed. The input means 19 also includes a plotter 30, which in response to a corresponding actuation the keyboard 18 is available instead of the monitor 20 for a graphic portrayal of the curvature 25 of the slice to be exposed which has been inputted into the system or installation.

For the inputting of a curvature 25 of a slice to be exposed using the "computer graphic tablet" this curvature is recorded with a writing pen 31 on a sheet of paper 32 placed on the "computer graphic tablet" 28. The pressure of the writing pen 31 will actuate pressure sensors situated in the surface of the "computer graphic tablet" 28, and these pressure sensors forward electrical signals to the input-output controller 23 which correspond to the curvature 25 of the slice to be exposed. In the case of the digitizer 29, the course or curvature 25 of the slice to be exposed occurs by contrast in that a graphic original or model of this curvature is traced with a sensing pen 33, wherein movement of the pen is converted into corresponding electrical signals which are supplied to the input-output controller 23. From the input-output controller 23, signals corresponding to the input curvature 25 of the slice to be exposed will proceed to the computation means 26 which converts them into data for the control means 16 and forwards them to the memory 27.

The computation means 26 is also constructed so that it is in the position to identify the sharply imageable slice thicknesses which belong to an input curvature 25 of the slice to be exposed. To this end, the computational means 26 is connected, first, to the output of the memory 27 and, secondly, to the central control unit 22 which in response to suitable actuation of the keyboard 18 supplies data of the curvature 25 of the slice to be exposed, which data is located in the memory 27, to the computational means 26 and initiates the latter to identify the corresponding curves 34 of the sharply imageable slice thickness and to supply these identified curves to the input-output controller 23 which then portrays them on the monitor 20 and/or the plotter 30.

FIG. 3 shows the block circuit diagram of another modification of a x-ray diagnostics installation of the present invention which modification initially differs from the installation of FIG. 2 in that the input means 19' for the input and for the graphical portrayal of the curvatures 25 of the slice to be exposed comprises only a monitor 20 with a light pen 21. In addition, a memory 27' is divided into two regions. One is fashioned as a write/read memory (RAM) and the other is fashioned as a read-only memory (ROM). Thus, the data of a plurality of curvatures 25 of slices to be exposed which are inputted with the light pen 21 can be stored in the write and read memory, whereas data of a plurality of standard curvatures of slices to be exposed are permanently stored in the read-only memory. In addition, the computation means 26 is constructed so that it can also process the data of the curvatures 25 of slices to be exposed which are present in the memory 27 in the sense of either a compression or an expansion respectively. This occurs in response to a suitable actuation of the keyboard 18. Then the central control unit 22 transfers the data of a specific curvature 25 from the memory 27 into the computation means 26 which then processes these in a manner which is selectable with the keyboard 18 and forwards them to the input controller 23 which portrays the original curvature 25 of the slices to be exposed on the monitor 20 in common with the curvature such as 25a which is derived therefrom. By suitable actuation of the keyboard 18, the input-output controller 23 can also be energized to simultaneously portray a plurality of curvatures present in the memory 27 or a plurality of curvatures derived therefrom by the computation means 26. This is an illustrated FIG. 3 by the curves 25, 25a, 25b, 25c, and 25d.

One of the curvatures 25a, 25b, 25c, 25d which are portrayed on the picture screen 24 of the monitor 20 can be transferred to the memory 27 by touching or tapping the selected curvature with a light pen 21. In the memory 27, this curvature is then available for the production of corresponding panoramic exposures. The production of the corresponding panoramic exposure is accomplished in the way set forth hereinabove.

The control means 16, the keyboard 18, the input means 19, the central control unit 22, the input-output controller 23, the computation means 27, and the memory 17 have been shown as individual functioning elements in FIGS. 2 and 3 and should be noted as conventional elements or devices. However, these can also be component parts of a data processing system, for example a small sized computer.

Although various minor modifications may be suggested by those versed in the art, it should be understood that we wish to embody within the scope of the patent granted hereon all such modifications as reasonably and properly come within the scope of our contribution to the art.

We claim:

1. In a dental x-ray diagnostics installation for the production of panoramic exposures of slices taken in a skull of a patient particularly those in the region of the jaw, said installation comprising an exposure unit with an x-ray tube being pivotable around an axis and displaceable in a plane extending perpendicular to the axis, a film holder unit lying opposite the exposure unit and movable relative thereto, support means including a head holder arranged between the two units for holding the head in a fixed position, control means for first controlling the pivoting and displacement motion of the exposure unit relative to the head holder of the support means, and for secondly controlling the movement of the film holder relative to the x-ray tube, the control means including input means for selecting a curvature of a slice to be exposed so that the control means can control the various movements in view of the selected curvature the improvements comprising said input means having a graphical input means with means for a human operator to graphically draw the selected curvature of a slice for the shape of the teeth and jaw of a patient as a continuous curved stroke and said graphical input means having means to directly input said graphically drawn selected curvature of a slice to the control means to control the relative movement of the exposure unit to the head holder and the relative movement of the film holder to the x-ray tube.

2. In a dental x-ray diagnostic installation according to claim 1, wherein the graphical input means comprises a computer graphics tablet.

3. In a dental x-ray installation according to claim 1, wherein the graphical input means comprises a monitor with a light pen.

4. In a dental x-ray diagnostic installation according to claim 1 wherein the graphical input means includes means for graphical portrayal of curvatures of slices to be exposed.

5. In a dental x-ray diagnostic installation according to claim 4, wherein the control means includes a memory for storage of data of one or more curvatures of slices to be exposed as stored curvatures, said memory supplying said stored curvatures to the graphical input means for graphical portrayal of the curvatures as well as through the remaining portions of the control means for controlling the production of the corresponding exposures.

6. In a x-ray diagnostic installation according to claim 5, wherein said memory has one part constructed as a read-only memory in which data of a plurality of standard curvatures of slices to be exposed is stored.

7. In a dental x-ray diagnostic installation according to claim 4, wherein the means for graphical portrayal is capable of portraying a plurality of curvatures of slices to be exposed and includes means to shape one of the portrayed curvatures for the production of a corresponding exposure.

8. In a dental x-ray diagnostic installation according to claim 1 wherein the controls means includes computation means for converting a curvature of a slice to be exposed which is received by the graphical input means into digital data for the control means.

9. In a dental x-ray diagnostic installation according to claim 8, wherein said computation means can calculate a sharply imageable slice thickness of the curvature of said slice to be exposed and said means for graphical presentation of the graphical input means portrays the images of the slice thickness in addition to the actual curvature of the slice to be exposed.

10. In a dental x-ray diagnostic installation according to claim 8, wherein said computation means includes means for compressing and expanding a basic curvature for a slice to be exposed and said graphical input means portrays the modified curvature obtained from said computation means.

* * * * *